(12) United States Patent
Baniel et al.

(10) Patent No.: US 7,572,376 B2
(45) Date of Patent: Aug. 11, 2009

(54) PROCESS FOR PRODUCING 1,3-PROPANEDIOL

(75) Inventors: Avraham M. Baniel, Jerusalem (IL); Robert P. Jansen, Collinsville, IL (US); Asher Vitner, Jerusalem (IL); Anthony Baiada, Dagenham (GB)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 7 days.

(21) Appl. No.: 11/352,593

(22) Filed: Feb. 13, 2006

(65) Prior Publication Data

US 2006/0124545 A1 Jun. 15, 2006

Related U.S. Application Data

(63) Continuation of application No. 10/430,498, filed on May 6, 2003, now Pat. No. 7,056,439.

(51) Int. Cl.
*B01D 11/00* (2006.01)
*C07C 31/18* (2006.01)

(52) U.S. Cl. .............. 210/634; 210/639; 210/774; 210/806; 435/158; 568/868; 568/872

(58) Field of Classification Search .............. 210/634, 210/639, 774, 805, 806; 435/157–162, 243; 568/852, 868, 869, 872
See application file for complete search history.

(56) References Cited

U.S. PATENT DOCUMENTS

| | | | |
|---|---|---|---|
| 3,707,188 A | 12/1972 | Heckman | 166/247 |
| 5,008,473 A * | 4/1991 | Breitkopf et al. | 568/868 |
| 5,164,309 A * | 11/1992 | Gottschalk et al. | 435/158 |
| 5,254,467 A | 10/1993 | Kretschmann et al. | 435/158 |
| 5,304,691 A | 4/1994 | Arhancet et al. | 568/867 |

(Continued)

FOREIGN PATENT DOCUMENTS

WO  WO 96/18596  6/1996

(Continued)

OTHER PUBLICATIONS

Bruce et al., *Biotechnol. Prog.* 7:116-124 (1991).

(Continued)

*Primary Examiner*—Joseph W Drodge
(74) *Attorney, Agent, or Firm*—Williams, Morgan & Amerson, P.C.

(57) ABSTRACT

Disclosed herein are processes for the recovery of 1,3-propanediol from an aqueous feed stream. The present invention involves contacting an aqueous feed stream that comprises water, 1,3-propanediol, and at least one contaminant with at least one solvent extractant to form a mixture. The mixture is separated into a first phase and a second phase. The second phase comprises a majority of the water from the aqueous feed stream. The first phase comprises solvent extractant and at least some of the 1,3-propanediol that was present in the aqueous feed stream. The weight ratio in the first phase of 1,3-propanediol to any one contaminant present is greater than the weight ratio of 1,3-propanediol to the same contaminant in the aqueous feed stream prior to the aqueous feed stream being contacted with the solvent extractant. The first phase can be removed from the separated second phase in order to recover the 1,3-propanediol.

21 Claims, 7 Drawing Sheets

U.S. PATENT DOCUMENTS

| | | | | |
|---|---|---|---|---|
| 5,356,812 A | 10/1994 | Matsuyama et al. | ......... | 435/280 |
| 5,463,145 A | 10/1995 | Powell et al. | ............... | 568/867 |
| 5,527,973 A | 6/1996 | Kelsey | ...................... | 568/862 |
| 5,599,689 A | 2/1997 | Haynie et al. | ................. | 435/42 |
| 5,633,362 A | 5/1997 | Nagarajan et al. | ......... | 536/23.1 |
| 5,770,776 A | 6/1998 | Powell et al. | ............... | 568/862 |
| 5,821,092 A | 10/1998 | Nagarajan et al. | .......... | 435/158 |
| 6,013,494 A | 1/2000 | Nakamura et al. | .......... | 435/158 |
| 6,025,184 A | 2/2000 | Laffend et al. | ........ | 435/252.33 |
| 6,136,576 A | 10/2000 | Diaz-Torres et al. | ........ | 435/158 |
| 6,171,501 B1 | 1/2001 | Eyal et al. | ................... | 210/634 |
| 6,232,511 B1 | 5/2001 | Haas et al. | ................. | 568/862 |
| 6,342,464 B1 | 1/2002 | Arhancet et al. | .............. | 502/257 |
| 6,361,983 B1 | 3/2002 | Ames | ......................... | 435/158 |
| 6,406,895 B1 | 6/2002 | Defretin et al. | ............ | 435/158 |
| 6,428,767 B1 | 8/2002 | Burch et al. | ............... | 424/1.37 |
| 6,428,992 B1 | 8/2002 | Roturier et al. | ............. | 435/158 |
| 6,469,222 B2 | 10/2002 | Knifton et al. | .............. | 568/867 |
| 6,479,716 B2 | 11/2002 | Hilaly et al. | ................ | 568/872 |
| 6,514,733 B1 | 2/2003 | Emptage et al. | ............. | 435/158 |
| 6,576,450 B2 | 6/2003 | Skraly et al. | ................ | 435/135 |
| 6,706,503 B2 | 3/2004 | Schellenberger et al. | .... | 435/170 |
| 6,942,803 B2 * | 9/2005 | Cockrem et al. | ............ | 210/639 |
| 7,056,439 B2 * | 6/2006 | Baniel et al. | ................ | 210/634 |
| 2002/0164729 A1 | 11/2002 | Skraly et al. | ................ | 435/135 |
| 2004/0262221 A1 * | 12/2004 | Herold et al. | ............... | 210/634 |

FOREIGN PATENT DOCUMENTS

WO     WO 01/73097 A2     10/2001

OTHER PUBLICATIONS

Laane et al., *Biotech. Bioengin.* 30:81-87 (1987).
Malinowski, *Biotechnology Techniques* 13:127-130(1999).

\* cited by examiner

PROCESS FOR PRODUCING 1,3-PROPANEDIOL

This is a continuation of application Ser. No. 10/430,498, filed May 6, 2003, now U.S. Pat. No. 7,056,439.

BACKGROUND OF THE INVENTION

1. Field of the Invention

The present invention relates generally to processes for producing and recovering 1,3-propanediol. More particularly, it concerns methods that rely on solvent extraction for production and recovery of 1,3-propanediol.

2. Description of Related Art

Purified 1,3-propanediol (PDO) can be produced commercially by methods known in the art that can involve fermentation, chemical, and mechanical separation processes. It is possible to produce 1,3-propanediol by fermentation, and production in this way requires methods of purifying 1,3-propanediol by targeting the removal of impurities that are the result of fermentation. When PDO is produced by fermentation the broth can contain a number of compounds such as glycerol and 1,2,4-butanetriol, which are very similar in chemical composition and properties to PDO. Glucose, a material that can be used to feed fermentation, is a compound that also has similarities to 1,3-propanediol, and residual amounts of glucose can remain after fermentation. A disadvantage of the fermentation route using glucose for the production of 1,3-propanediol is that sugars such as glucose will create color in downstream processes involving heat, such as distillation and evaporation. Preferably the residual glucose is separated from the PDO to purify the PDO. There is a need for a process to separate 1,3-propanediol from impurities in addition to sugars that will result in greater purity of the PDO, and that can eliminate or reduce the amount of energy intensive distillation (e.g., a common method of purifying PDO) required to produce the purified PDO.

SUMMARY OF THE INVENTION

Certain embodiments of the present invention are directed to processes for the recovery of 1,3-propanediol from an aqueous feed stream. The aqueous feed stream comprises water, 1,3-propanediol and at least one contaminant. Preferably the aqueous feed stream comprises a fermentation broth that is concentrated and/or partially purified. In certain preferred embodiments, the aqueous feed stream comprises between about 5 wt % to 85 wt % 1,3-propanediol, and further comprises greater than about 10 wt % water, and between about 5 wt % to 70 wt % of one or more of the contaminants. In certain embodiments, the aqueous feed stream comprises up to 90 wt % dry solids. Preferably the feed stream comprises between about 20 wt % and 80 wt % dry solids. The at least one contaminant present in the aqueous feed stream is preferably a compound selected from the group consisting of organic acids, organic salts, inorganic salts, carbohydrates, alcohols, proteins, amino acids, and low molecular weight hydroxylated compounds. A low molecular weight hydroxylated compound can be selected from the group consisting of glycerol, glucose, and butanetriol. Preferably the aqueous feed stream has a pH of between about 2 and 11, more preferably between about 6 and 8.

The aqueous feed stream is contacted with at least one solvent extractant to form a first mixture. The contacting of the solvent extractant and the aqueous feed stream can be performed counter current, cross current, or counter cross current, as explained below. The contacting can be performed using more than one stage, as is known in the art for the contacting of two liquids. In certain embodiments the solvent extractant is essentially anhydrous (e.g., comprising less than about 0.5 wt % water), and in others it is saturated with water. Preferably the at least one solvent extractant is selected from the group consisting of alcohols, ketones, esters, acids, ethers or vegetable oils with hydrophobic parameter log P (log P=[solute]octanol/[solute]water) of between about 0.8 and 7.7. In certain preferred embodiments the solvent extractant has a hydrophobic parameter of between about 0.8 and 2.9. (Biotechnology and Bioengineering Vol. 30, pages 81-87, July 1987; Biotechnol. Prog., Vol. 7 No. 2) In certain embodiments the solvent extractant is selected from the group consisting of (I) alkanols such as pentanol, propan-1-ol, hexanol, or oleyl alcohol, (2) ketones like 4-methyl pentan-2-one, (3) esters like isopropyl acetate or tributyl phosphate, (4) acids like oleic acid (5) oils like soya oil, or castor oil, and (6) ethers. Preferably the solvent extractant is hexanol or tributylphosphate. In certain embodiments the solvent extractant has a carbon to oxygen atom ratio of between about 2:1 and 18:1, more preferably 2:1 and 10:1 and most preferably 3:1 and 6:1.

In certain embodiments a phase enhancer selected from aliphatic and aromatic hydrocarbons can be used in addition to solvent extractants (such as those taught above) in order to enhance phase separation. Preferred phase enhancers are alkanes in the range from hexane to decane (e.g., having from 6 to nine carbon atoms).

The first mixture is separated into a first phase and a second phase. The first phase comprises a majority (e.g., greater than about 50%) of the solvent extractant and at least some of the 1,3-propanediol that was present in the aqueous feed stream. The weight ratio in the first phase of 1,3-propanediol to any one contaminant present is greater than the weight ratio of 1,3-propanediol to the same contaminant in the aqueous feed stream prior to the aqueous feed stream being contacted with the solvent extractant. Thus, the 1,3-propanediol in the first phase is purer than the 1,3-propanediol in the aqueous feed stream. The second phase comprises a majority (e.g., greater than about 50 wt %) of the water from the aqueous feed stream, and at least some of the contaminant from the aqueous feed stream. The separation can be performed using methods known in the art. In certain embodiments, the contacting step and separation of the first phase and the second phase are carried out in a mixer-settler. In certain preferred embodiments the first phase is separated from the second phase using a centrifuge. In certain embodiments purified 1,3-propanediol is recovered by removing the first phase from the second phase. Certain embodiments of the present invention are preferably carried out a temperature between about 20° C. and 90° C., more preferably between about 25° C. and 35° C., and most preferably at a temperature of about 30° C.

In certain embodiments, the removed first phase is contacted with a first quantity of aqueous solution or water to form a second mixture. The volume ratio of the first quantity of water or aqueous solution to the first phase is between about 20:1 and 1:20, more preferably between about 20:1 and 1:1, and most preferably about 7:1 and 3:1. The second mixture is separated into a third phase and a fourth phase. The third phase comprises a majority (e.g., greater than about 50 wt %) of solvent extractant of the first phase. The fourth phase comprises 1,3-propanediol and a majority (e.g., greater than about 50 wt %) of the first quantity of aqueous solution or water. The weight ratio in the fourth phase of 1,3-propanediol to any one contaminant present is greater than the weight ratio of 1,3-propanediol to the same contaminant in the aqueous feed stream prior to the aqueous feed stream being contacted with the solvent extractant. Thus, the 1,3-propanediol in the fourth phase is purer than the 1,3-propanediol in the aqueous feed stream. The separation can be performed using methods known in the art for separation of two immiscible or partially miscible liquids. In certain embodiments purified 1,3-propanediol is recovered by removing (e.g., by decantation) the fourth phase from the third phase. In certain embodiments, the recovered third phase can be recycled to the solvent extractant used in the first mixture. The recovered fourth phase can be treated to further purify the 1,3-propanediol in the fourth phase. The fourth phase can be recycled such that the aqueous feed stream for the first mixture comprises the recovered fourth phase.

In certain embodiments, the removed first phase further comprises at least some water in addition to the 1,3-propanediol and solvent extractant, and the removed first phase is contacted with a hydrophobic solvent to form a second mixture. Preferably the weight ratio of the removed first phase to the hydrophobic solvent in the second mixture is between about 4:1 to 1:4, preferably 2:1 to 1:2. Preferably the hydrophobic solvent is selected from solvents with log P of between about 3.0 and 10, preferably 3.5 to 5.5. Preferably the hydrophobic solvent is selected from alkanes in the range having molecular weights between hexane and that of dodecane. The second mixture is separated into a third phase and a fourth phase. The third phase comprises the majority (e.g., greater than about 50 wt %) of both the solvent extractant and the hydrophobic solvent of the second mixture. The fourth phase comprises 1,3-propanediol and the majority (e.g., greater than about 50 wt %) of the water of the first phase. Preferably the weight ratio in the fourth phase of the 1,3-propanediol to any one contaminant present is greater than the weight ratio of the 1,3-propanediol to the same contaminant in the aqueous feed stream prior to the aqueous feed stream being contacted with the solvent extractant. Thus, the 1,3-propanediol in the fourth phase is purer than the 1,3-propanediol in the aqueous feed stream. The 1,3-propanediol can be recovered by removing the fourth phase from the third phase.

Certain processes of the present invention involve adjusting the temperature of the first mixture during the contacting step such that 1,3-propanediol is more soluble in the solvent extractant than in the aqueous feed stream and the solvent extractant is hexanol. The first mixture of the aqueous feed stream and the solvent extractant is separated into the first phase and the second phase, as described above. The first phase is removed from the second phase. The temperature of the first phase is adjusted such that a second mixture is formed. The second mixture is separated into a third phase and a fourth phase. The third phase comprises a majority of the hexanol from the first phase, and the fourth phase comprises 1,3-propanediol. Preferably the weight ratio in the fourth phase of 1,3-propanediol to any one contaminant present is greater than the weight ratio of 1,3-propanediol to the same contaminant in the aqueous feed stream prior to the aqueous feed stream being contacted with the solvent extractant.

Certain methods known in the art for purification of PDO from an aqueous feed (i.e., fermentation broth) comprising contaminants involve extracting contaminants while leaving the PDO in the aqueous feed stream. Certain methods of the present invention involve extracting the PDO from the aqueous feed stream, into a solvent phase away from contaminants present in the feed. Certain embodiments of the present invention can increase the purity of 1,3-propanediol from impure feed streams.

DESCRIPTION OF ILLUSTRATIVE EMBODIMENTS

Figure 1:
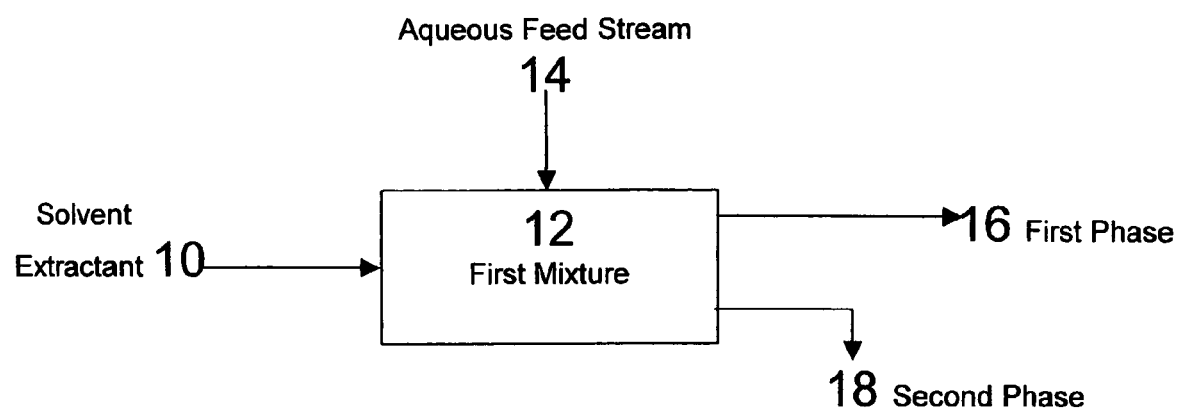
FIG. 1 is a process flow diagram in accordance with the present invention for recovery of 1,3-propanediol.

FIG. 1 is a schematic of a process of the present invention. An aqueous feed stream (e.g., a fermentation broth) 14 comprising water, 1,3-propanediol and at least one contaminant is contacted with solvent extractant 10 in an extractor 12 to form a first mixture. The solvent extractant is preferably immiscible or partially miscible with water over a range of temperatures (e.g., 2° C. and 100° C.). The volume/volume ratio of solvent extractant 10 to aqueous feed stream 14 (e.g., filtered fermentation broth, as described below) is preferably between 1:4 and 50:1, more preferably about 10:1. In certain preferred embodiments the solvent extractant has a hydrophobic parameter log P (log P=[solute]octanol/[solute]water) of between about 0.8 and 7.7, and more preferably 0.8 and 2.9 such as those listed in the table below. A preferred solvent extractant is tri-butyl phosphate (TBP).

| ethyl acetate | 0.68 |
| propyl acetate | 1.2 |
| hexanol | 1.8 |
| TBP (estimated) | 2.0 |
| heptanol | 2.4 |
| octanol | 2.8 |

The aqueous 1,3-propanediol feed stream 14 and the solvent extractant (e.g., TBP) 10 are agitated at a temperature between about 2° C. and 100° C., more preferably 30° C. After agitation the combined mixture can be allowed to settle and separate into two phases. A first phase 16 comprises a majority (e.g., greater than about 50 wt %) of the solvent extractant, and a second phase 18 comprises a majority (e.g., greater than about 50 wt %) of the water present in the first mixture 12. The first phase comprises at least some of the 1,3-propanediol that was present in the aqueous feed stream 14 and the weight ratio of the 1,3-propanediol to any one contaminant present in the first phase is greater than the weight ratio of the 1,3-propanediol to the same contaminant in the aqueous feed stream 14 prior to the aqueous feed stream being contacted with the solvent extractant 10. The first phase 16 can be separated and removed from the second phase 18 to recover 1,3-propanediol by methods known in the art (e.g., centrifugation and decantation, among others.) The recovered 1,3-propanediol is purer (e.g., have relatively less contaminant per amount of 1,3-propanediol present) than the starting aqueous feed stream.

The first phase 16 comprises 1,3-propanediol and solvent extractant, and the majority (e.g., greater than about 50 wt %) of the 1,3-propanediol can be transferred back (e.g., back extracted) to an enriched aqueous phase by several methods. The back extraction process can in certain embodiments involve known mixer-settler systems or centrifugal systems. Back extraction can be accomplished by several methods. These include use of water or aqueous solution (FIG. 2), use of a second solvent that is hydrophobic (FIG. 3), or use of a change in temperature (FIG. 4).

Figure 2:
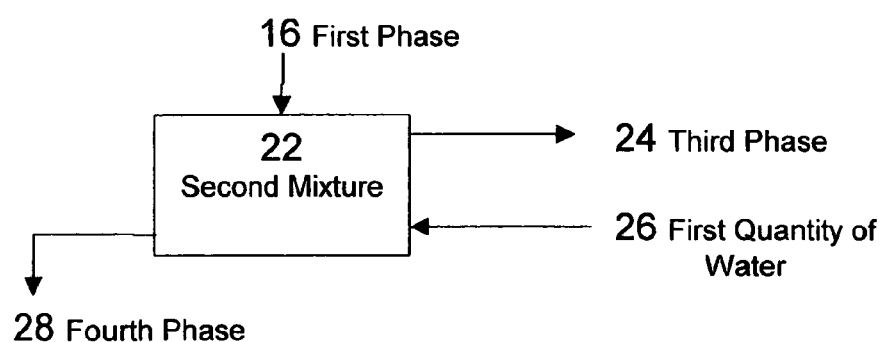
FIG. 2 is a process flow diagram in accordance with the present invention for recovery of 1,3-propanediol with back extraction involving water.

Back extraction with water or an aqueous solution is shown in FIG. 2. A first quantity of water or aqueous solution 26 is contacted with a first phase 16, as described above to form a second mixture 22. The first quantity of water 26 can be contacted with the first phase 16 at a range of temperatures from about 2° C. to 100° C., preferably 30° C. The first quantity of water 26 to first phase 16 can be between about 20:1 to 1:20 v/v, but is preferably about 3:1 v/v. At least some of the 1,3-propanediol transfers from the first phase 16 to a fourth aqueous phase 28, and this can be removed, for example, from a settler by decantation leaving a third solvent extractant phase 24, which can be recycled for further extraction processes (e.g., recycled to solvent extractant). The third phase 24 comprises a majority (e.g., greater than about 50 wt %) of the solvent extractant from the second mixture. The fourth phase 28 comprises a majority (e.g., greater than about 50 wt %) of the water from the second mixture. In certain embodiments, a centrifuge can also be used to separate the aqueous phase 28 from the solvent extractant phase 24. The weight ratio in the fourth phase 28 of the 1,3-propanediol to any one contaminant present is greater than the weight ratio of 1,3-propanediol to the same contaminant in the aqueous feed stream prior to the aqueous feed stream being contacted with the solvent extractant.

Figure 3:
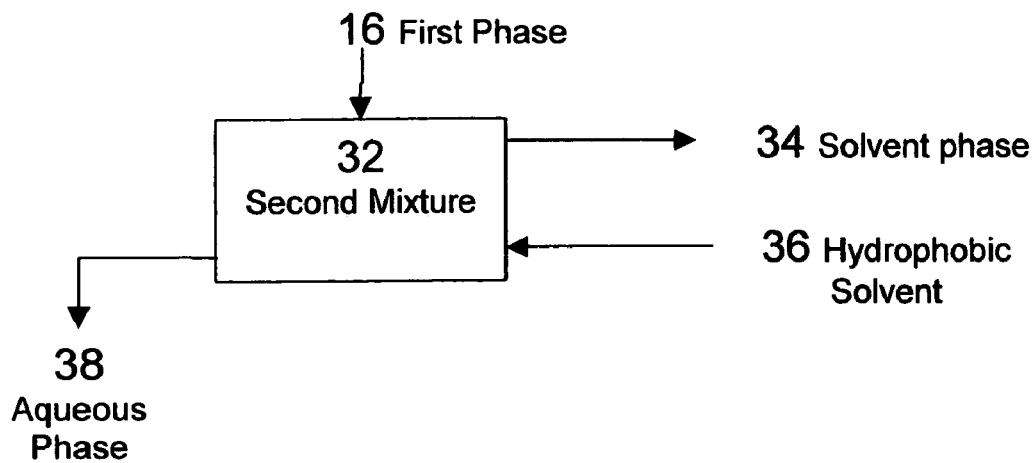
FIG. 3 is a process flow diagram in accordance with the present invention for recovery of 1,3-propanediol with back extraction involving a hydrophobic solvent.
Figure 4:
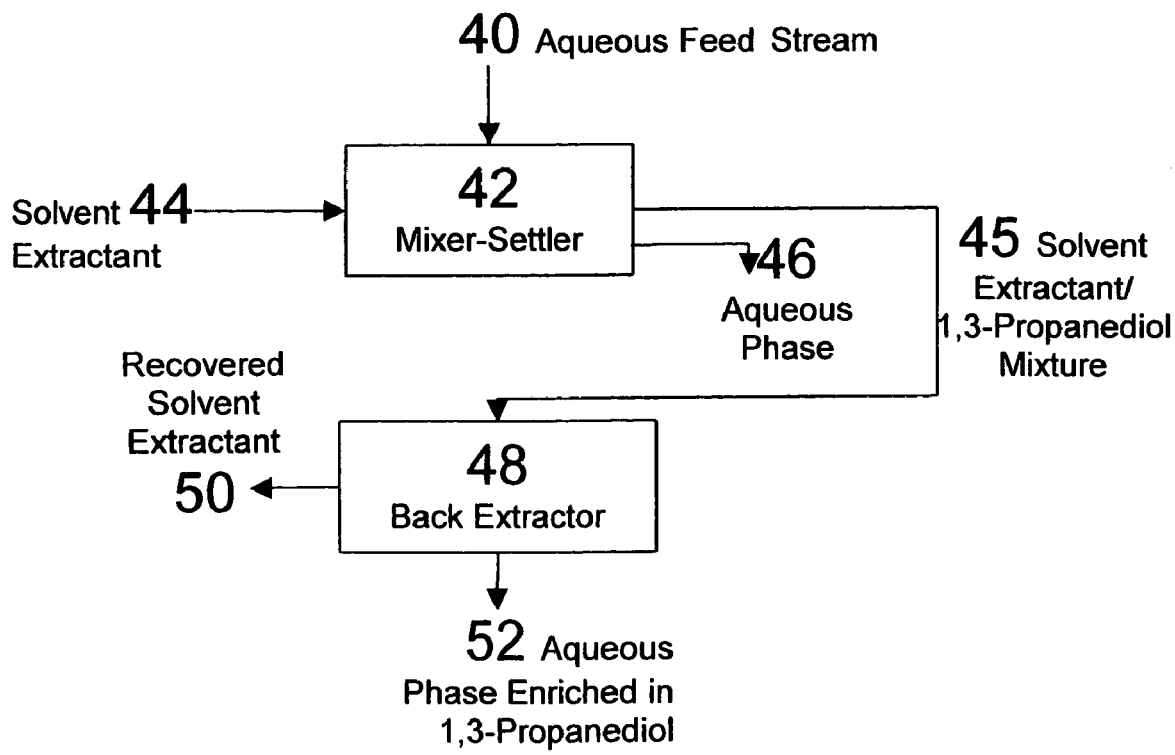
FIG. 4 is a process flow diagram in accordance with the present invention for recovery of 1,3-propanediol with back extraction involving a change in temperature.

An alternate way of accomplishing back extraction is with a hydrophobic solvent, and this is shown in FIG. 3. Preferably the hydrophobic solvent is selected from solvents with log P of between about 3.0 and 5.5, such as those in the table below. Preferred hydrophobic solvents are alkanes in the range from hexane to decane.

| | |
|---|---|
| decanol | 4.0 |
| dodecanol | 5.0 |
| hexane | 3.5 |
| heptane | 4.0 |
| octane | 4.5 |
| decane | 5.98 |
| Soy oil | 7.4 |

The first phase 16 comprising 1,3-propanediol, solvent extractant, and at least some water can be contacted with a hydrophobic solvent 36 (e.g., hexane) to form a second mixture 32, and the mixture 32 can be allowed to settle to form two phases. The contacting and settling can be performed in mixer-settler equipment. In certain embodiments, the two phases can be separated in a centrifugal device. One of the two phases is a solvent phase 34 comprising a majority (e.g., greater than about 50 wt %) of the solvent extractant and the hydrophobic solvent, and the other phase is an aqueous phase 38 enriched in 1,3-propanediol that was transferred from the first phase 16. The aqueous phase 38 is comprised of a majority of the water (e.g., greater than about 50 wt %) and 1,3-propanediol that was present in the first phase 16. A preferred ratio of first phase 16 to hydrophobic solvent 36 is between about 4:1 and 1:4, more preferably between about 2:1 and 1:2, in the back extraction with the hydrophobic solvent.

A third way of releasing the 1,3-propanediol from the solvent can be accomplished by extracting, and back extracting at different temperatures (FIG. 4). This can be done using, for example, hexanol as a solvent extractant 44. The aqueous feed 40 is brought into contact with hexanol at about 80° C. in a mixer-settler 42, and upon settling the aqueous phase 46 (e.g., comprising water from the aqueous feed stream) with the impurities is discarded. The hexanol/1,3-propanediol mixture 45 that is removed at 80° C. is cooled to about 30° C., whereupon the material will separate into two phases in the back extractor 48. One phase 50 comprises hexanol and can be recycled. The other phase 52 comprises water, and is enriched in 1,3-propanediol. A preferred weight ratio of aqueous feed at 30% d.s. to hexanol solvent would be about 1:3

The processes depicted in FIGS. 1 through 4 can increase the propane-1,3-diol content of a fermentation broth or other aqueous feed stream, calculated on a water-free basis, from about 85% to over 99% by weight, and the 1,3-propanediol can be much purer than in the starting feed stream.

Figure 5:
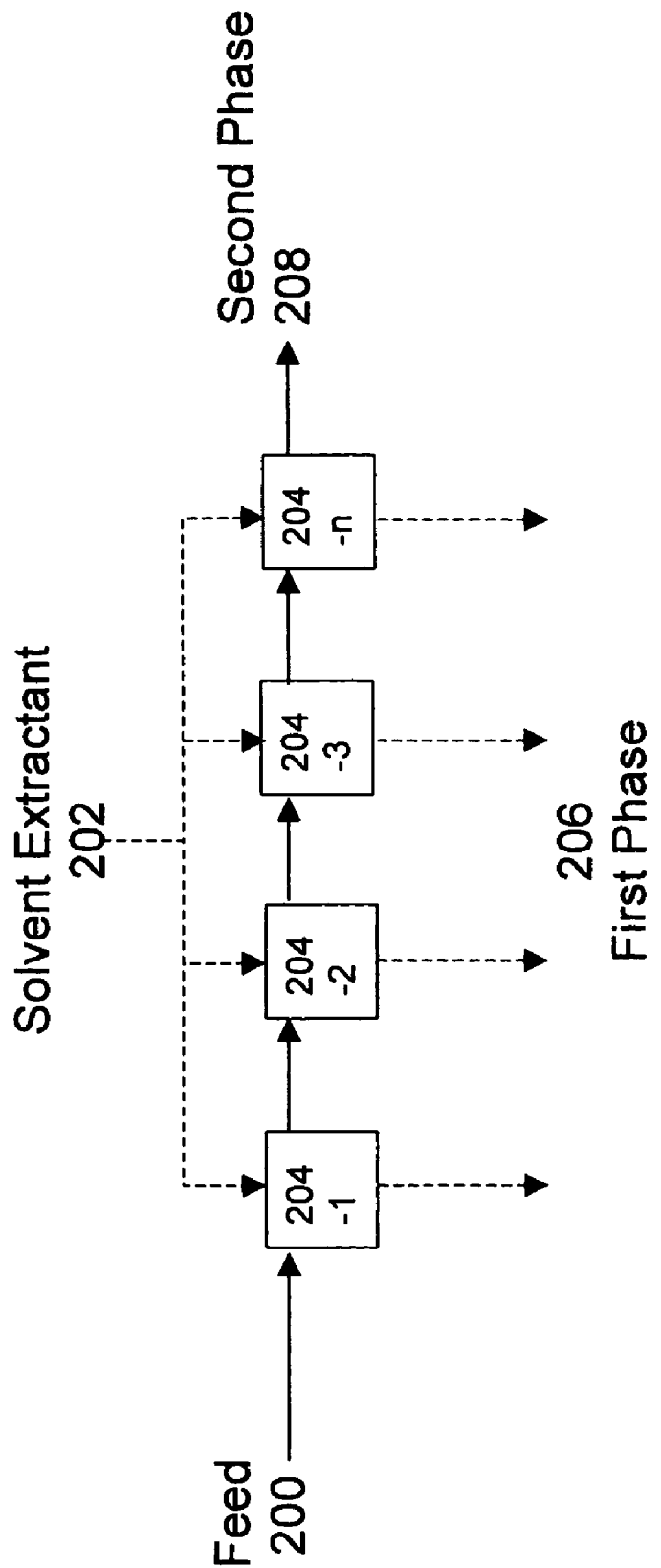
FIG. 5 is a process flow diagram of cross current contacting of a feed stream and a solvent extractant for extraction of 1,3-propanediol.

The contacting of the 1,3-propanediol and the solvent can be carried out in one stage, or in multiple stages. Treatment with a number of stages (e.g., from 1 to n) increases the effectiveness of the transfer of the 1,3-propanediol from one phase to the other phase. There are a number of ways of using multiple stages. For example, a cross-current arrangement set up (FIG. 5), as is known in the art, can be used for an extraction. There can be any number of stages from 1 to n with each stage representing mixing and separation (e.g., mixer settlers, 204-1, 204-2, 204-3, 204-n). Fresh solvent extractant 202 is fed into each stage 204-1, 204-2, 204-3, 204-n, whereas the feed material 200 containing 1,3-propanediol passes through each stage 204-1, 204-2, 204-3, 204-n in turn. In each stage there are two phases and the fraction with solvent containing 1,3-propanediol (e.g., first phase 206) can be removed at each stage. Usually these fractions can be combined. Each stage can be provided with the means for internal recycle of the solvent extractant 202 or the second phase 208 so that the proportion of the phases can be optimized for coalescence and separation characteristics.

Figure 6:
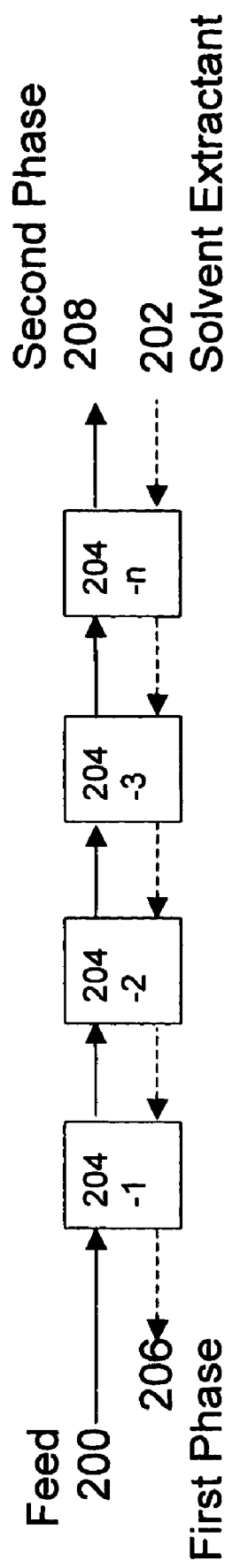
FIG. 6 is a process flow diagram of counter current contacting of a feed stream and a solvent extractant for extraction of 1,3-propanediol.

Alternatively a counter-current arrangement (FIG. 6), as is known in the art, can be used for extraction. This can have any number of stages from 1 to n, and each stage represents mixing and separation (e.g., mixer settlers, 204-1, 204-2, 204-3, 204-n). The aqueous feed 200 containing 1,3-propanediol and the solvent extractant 202 are passed in opposite directions through the stages 204-1, 204-2, 204-3, 204-n, with the depleted feed (e.g., second phase 208) leaving the last stage 204-n, and the first phase 206 leaving stage 204-1. Also in this configuration each stage 204-1, 204-2, 204-3, 204-n can be provided with the means for internal recycle of the solvent extractant 202 or the second phase 208 so that the proportion of the phases can be optimized for coalescence and separation characteristics.

Figure 7:
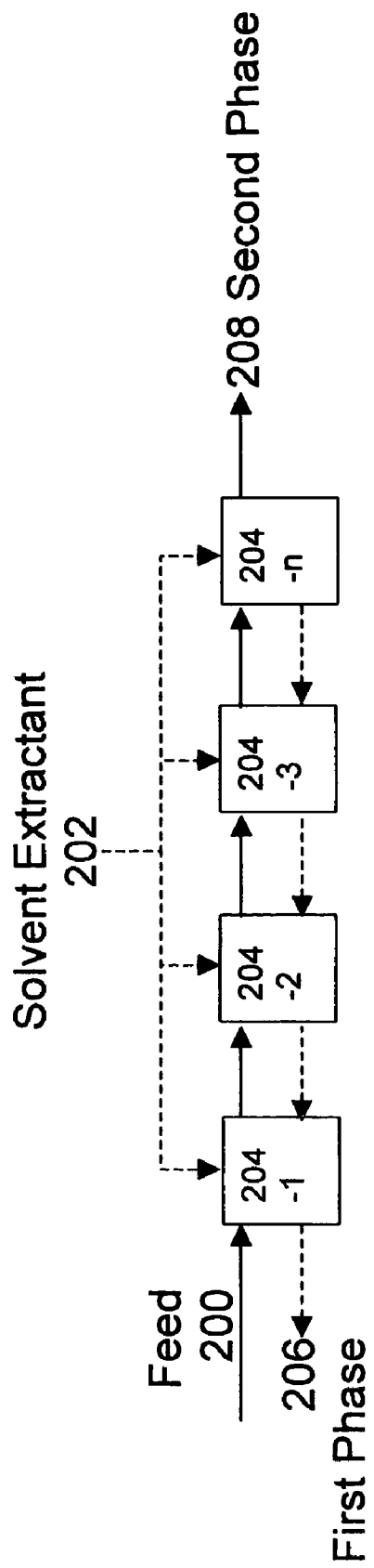
FIG. 7 is a process flow diagram of counter cross current contacting of a feed stream and a solvent extractant for extraction of 1,3-propanediol.

Another possible method of extraction can involve counter cross current (as is known in the art, FIG. 7) of the aqueous feed stream 200 and the solvent extractant 202. In this method, fresh solvent extractant 202 can be added into any of the stages 1 to n 204-1, 204-2, 204-3, 204-n, but the first phase 206 is passed counter-current from stage 204-n and withdrawn at stage 204-1, with the depleted feed (e.g., second phase 208) leaving the last stage n.

Figure 8:
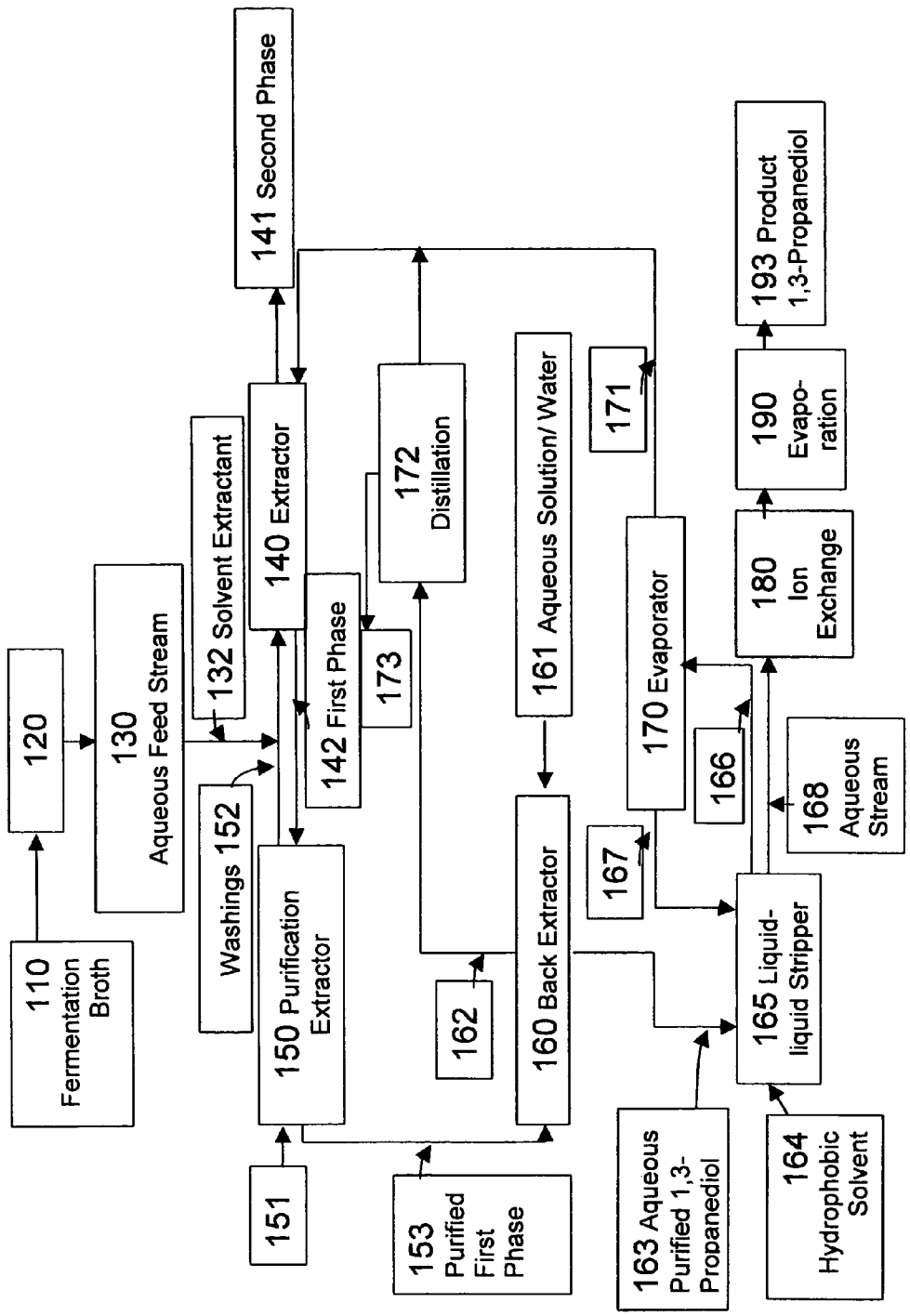
FIG. 8 is a process flow diagram in accordance with the present invention for recovery of 1,3-propanediol.

FIG. 8 is a more detailed schematic of a process of the present invention. A fermentation broth produced by fermentation or other aqueous feed comprising 1,3-propanediol 110 comprises at least one contaminant that can be selected from organic acids or salts thereof, inorganic salts, protein fragments, ketones, metal ions, cells, cellular debris, fermentation products (e.g., glycerol, and 1,2,4-butanetriol, among others), color impurities, water, nutrients (e.g., ammonia and phosphate, among others), and unused carbon source (e.g., glucose). A fermentation seed stock can be generated using a fermentation seed train. The fermentation seed stock is introduced into a fermentation for the production of 1,3-propanediol, along with fresh nutrients, water, and a carbon source. Methods of fermentation are known in the art. The cell culture is then processed to recover the fermentation broth 110. The present invention provides means for recovering 1,3-propanediol from fermentation broth. However, it should be understood that the present invention is not limited to use in conjunction with fermentation, nor is it limited to use with broth that has been purified, and/or concentrated, as pointed out below.

Preferably at least about 75 wt % of the solids (e.g., cells and cellular debris) in the fermentation broth 110 are removed by filtration or centrifugation methods 120 known in the art (e.g., rotary vacuum filter or vacuum belt filter). More preferably at least about 90 wt % of the solids in the fermentation broth 110 are removed, most preferably at least about 95 wt %. The dry solids content of the filtered fermentation broth is preferably between about 8 and 20% dry solids (d.s.), more preferably about 15% on a dry solids basis. The filtered fermentation broth 120 can optionally be concentrated by removal of water in an evaporator 130, resulting in a broth preferably having 30 to 50% d.s., more preferably about 40% d.s.

The fermentation broth 110, 120 can undergo partial purification and/or pre-treatment prior to recovery of 1,3-propanediol using methods known in the art. Partial purification can, for example, comprise precipitation and removal of certain impurities.

A solvent extractant 132 comprising one or more solvents can be contacted in an extractor 140 with the filtered and optionally concentrated fermentation broth 130. One preferred solvent extractant is tri-butyl phosphate (TBP). The solvent extractor 140 can be in a number of stages using counter-current flow, counter cross-current flow, cross-current flow, mixer-settlers or centrifugal contacting devices, or other devices commonly used for liquid—liquid extraction. The extraction system 140 can be just one stage, but for efficient operation giving good yield it is preferable to use multiple stages. A typical ratio of feed (e.g., filtered and optionally concentrated fermentation broth) at 40% d.s. to solvent extractant used in extraction is about 1:10.

The second phase 141 comprising water will comprise most of the sugars, salts and at least some of the glycerol and other impurities that were present in the filtered broth 130. The sugars, salt and glycerol (e.g., raffinate) can be discarded 141, or purified further if desired.

The first phase 142 comprising the solvent extractant comprises 1,3-propanediol, extracted from the feed stream 130 by the solvent (preferably TBP) along with some of the impurities present in the aqueous feed stream 130. This can be purified further in a purification extractor 150 by using a wash with a limited quantity of aqueous solution or water 151. Optionally, the aqueous solution 151 can comprise a dilute base such as caustic soda, to remove some color and organic acids from the first phase 142. The quantity of water or dilute base (e.g., aqueous solution) used at this stage is typically at a ratio to the first phase of 1:15, but is always less than the amount used in the back-extraction 160. The aqueous phase 152 from the purification extractor 150, which is a stream containing the washings from the purification stage, can be mixed with the solvent extractant 132. The purpose of the purification step 150 is to wash the remaining impurities from the first phase, giving a high degree of purification. The impurities will contain some 1,3-propanediol, but this can be recovered when the washings 152 are recycled to the extraction step 140.

The purification extractor 150 is a liquid-liquid extraction unit and can be, for example, mixer-settlers or centrifugal contactors. The number can range from one to multiple units, depending on the effectiveness of purification required.

The purified 1,3-propanediol in the solvent extractant (such as TBP), 153, is termed the purified first phase and comprises solvent extractant. The next step is to send the purified first phase 153 to a back extraction unit 160. This unit applies water 161 in sufficient quantity to transfer the 1,3-propanediol from the purified first phase 153 into the water phase 163. The back extractor 160 is preferably a liquid-liquid contacting unit, and can be a mixer-settler, a column extractor, or a centrifugal contacting device, for example. There can be one stage or multiple stages depending on the effectiveness of back-extraction required. The ratio of water 161 to purified first phase 153 is preferably 1:4. The 1,3-propanediol is transferred to the heavy, aqueous phase 163. The stream comprising solvent extractant (e.g., TBP) 162 from the back extraction unit 160, can be recycled to the extraction unit 140. Optionally, the water can be removed from this solvent extractant stream 162 by distillation 172, and the water 173 discarded. About 6% water can dissolve in TBP (e.g., solvent extractant) at certain temperatures used, and removal of this water 173 to get dehydrated solvent extractant can improve the effectiveness of extraction in the extractor 140.

TBP that can be used in the present invention is partially soluble in water. The remaining solvent can be removed from the aqueous stream 163 that contains purified 1,3-propanediol by treatment with a hydrophobic solvent 164, such as hexane, in a liquid-liquid extraction stripper unit 165. The hydrophobic solvent stream 164 (e.g., hexane) will separate solvent extractant from the water, leaving the 1,3-propanediol in water with virtually no dissolved or entrained solvent extractant. This stripper 165 can be a mixer-settler or a centrifugal contactor, and there can be one or multiple stages, depending on the effectiveness required. The typical ratio of aqueous product stream to hydrophobic solvent stream (e.g., hexane) is 50:1.

The mixed solvent stream 166 contains a mixture of hydrophobic solvent (e.g., hexane) and solvent extractant (e.g., TBP), and these can be separated by distillation in an evaporator 170. The hydrophobic solvent 167 separated by this distillation evaporation can be returned to the liquid-liquid stripper unit 165, and the solvent extractant 171 recycled to the extraction unit 140.

The aqueous stream 168 from the stripper 165, can be evaporated 190 to produce the product 1,3-propanediol 193. Optionally ion exchange treatment 180 using, for example, a mixed bed column with a mixture of strong acid cation and strong base anion resins can be used, either before or after the evaporation stage 190, in order to remove color and some organic acids such as levulinic acid, as a further purification. Preferably the purity of the 1,3-propanediol 193 can be over 99% by weight, and a high yield of 1,3-propanediol is possible using this process.

Recovery of 1,3-propanediol from a complex aqueous feed (e.g., fermentation broth) in the present invention can result in the selective transfer of 1,3-propanediol to a solvent extractant phase. In certain embodiments, the solvent extraction of the present invention can be used to separate a few, specific impurities along with PDO from a complex aqueous feed stream comprising PDO and impurities. Certain contaminants, which can be present in an aqueous feed (e.g., fermentation broth) comprising PDO are chemicals of the same chemical class as PDO (e.g., low molecular weight hydroxylated compounds). Contaminants that are in the same class as PDO, with log P in the range of −2.1 to 1 are for example glycerol, butanetriol, or glucose. (See examples in the table below.)

| | |
|---|---|
| glycerol | −2.08 |
| 1,4 butanediol | −1.384 |
| 1,2 PDO | −1.003 |
| ethanol | −0.24 |

Compounds in the class of low molecular weight hydroxylated compounds, such as PDO, tend to interact strongly with water, and are often completely miscible with water. Methods known in the art can require high energy input (e.g., in distillation) to separate water from these compounds, as these compounds interact strongly with water and are miscible with water. Thus, the fact that 1,3-propanediol and related compounds can be recovered in a water-immiscible solvent, as in the present invention is surprising. It is even more surprising that the PDO can be selectively extracted over compounds of the same class. Thus, selective extraction of PDO from aqueous feed into water-insoluble (e.g., castor oil) or low-miscibility (e.g., TBP and hexanol, among others) solvents as in present invention was unexpected.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Single Stage Extractions and Back Extractions of 1,3-Propanediol

EXAMPLE 1a

Extraction with Tributyl Phosphate 4.2 ml of a concentrated aqueous fermentation broth containing 31.33% w/v 1,3-propanediol (PDO), 1.66% Glycerol, 0.74% 1,2,4 butanetriol (BTO) and 0.13% glucose was thoroughly mixed with 35 ml of tributyl phosphate (containing 6% water) at 20° C. The mixture was separated with the aid of centrifugation into two phases (37 ml of Light 1 phase (e.g., first phase) and 2.5 ml of Heavy 1 phase (e.g., second phase)). The Light 1 phase comprising the tributyl phosphate (4 ml) was purified by mixing with 0.24 ml of water and allowed to separate to give a Heavy 2 phase comprising water (0.3 ml) and a "purified" Light 2 phase comprising tributyl phosphate (3.7 ml).

EXAMPLE 1b

Back Extraction with Water

The purified Light 2 phase comprising tributyl phosphate (3 ml) was back extracted with 11.5 ml of water by mixing and separating the phases, to give Light 3 phase comprising tributyl phosphate (3 ml) and Heavy 3 phase comprising water (11.5 ml).

EXAMPLE 1c

Back Extraction with Hexane 2 ml of the purified Light 3 phase was back extracted with n-hexane (6 ml) by mixing and separating the phases to give Light 4 phase comprising hexane (5.8 ml) and Heavy 4 phase comprising water (0.2 ml). Table 1 shows the compositions of the streams encountered in this example.

TABLE 1

| | Phase Composition % w/v | | | | % Purity |
|---|---|---|---|---|---|
| | PDO | Glycerol | BTO | Glucose | PDO |
| Feed Broth | 31.33 | 1.66 | 0.74 | 0.13 | 92.6 |
| Extraction with TBP | | | | | |
| Light 1 | 2.38 | 0.06 | 0.04 | 0.00 | 96 |
| Heavy 1 | 16.06 | 1.81 | 0.75 | 0.05 | |
| Purification with water | | | | | |
| Light 2 | 1.67 | 0.03 | 0.01 | 0.00 | 97.4 |
| Heavy 2 | 10.77 | 0.50 | 0.25 | 0.02 | |
| Back extraction with water | | | | | |
| Light 3 | 0.06 | 0.00 | 0.00 | 0.00 | |
| Heavy 3 | 0.46 | 0.01 | 0.00 | 0.00 | 97.3 |
| Back extraction with hexane | | | | | |
| Light 4 | 0.26 | 0.00 | 0.00 | 0.00 | |
| Heavy 4 | 8.5 | 0.26 | 0.15 | 0.00 | 96.3 |

PDO is 1,3-Propanediol
BTO is Butanetriol

The color of the fermentation broth fed to the extractions was brown. The first extraction gave a light yellow Light 1 phase, and a brown Heavy 1 phase. In the purification stage further color was removed from the Light 1 phase as shown by a darker yellow color of the Heavy 2 phase.

EXAMPLE 2

Change in Temperature During Extraction of 1,3-Propanediol 1,3-Propanediol (PDO) can be purified by extracting in hexanol, separating and then cooling the light solvent phase, and then separating the heavy aqueous phase that forms. Purer 1,3-propanediol will be present in this aqueous phase.

3 g of a mixture at 30% of dry solids, containing 1,3-propanediol to be purified and with a composition as in the table below was extracted in two stages at 90° C. The amount of fresh hexanol used in each stage was 12 g. The light phase from the second extraction was then used to extract PDO from 3 g of further 30% dry solids feed in a third extraction. The extractions and separations were all carried out in conical glass tubes of approximately 50 ml volume.

Each extraction was carried out for 20 minutes with periodic agitation. The light phase from the first extraction was discarded.

The analysis of the light phase for the third extraction is given in the table below. This light phase is then cooled to room temperature of 25° C. On cooling it splits to two phases and the newly formed aqueous heavy phase is separated, analyzed, and the results are in the table.

TABLE 2

| Feed | | | Light Phase 90° C. | | | Heavy Phase 25° C. | | | Selectivity | |
| --- | --- | --- | --- | --- | --- | --- | --- | --- | --- | --- |
| PDO | GLY | GLU | PDO | GLY | GLU | PDO | GLY | GLU | GLY/PDO | GLU/PDO |
| 24.2 | 1.86 | 0.46 | 6.03 | 0.16 | 0.00 | 28.3 | 1.69 | 0.03 | 1.3 | 18 |

Selectivity = [PDO/impurity] $_{heavy\ phase}$/[PDO/impurity] $_{feed}$. Impurity = GLY or GLU  GLY = Glycerol  GLU = Glucose

EXAMPLE 3

Cross Current Extractions of PDO

EXAMPLE 3a

Extraction with Anhydrous Tributyl Phospate

In a two stage cross-current extraction scheme, 5.0 g of an aqueous feed at 44% dry solids with the composition (% w/w on dry solids) 91.9% PDO, 6.9% glycerol and 1.2% glucose was thoroughly mixed at ambient temperature with 24.9 g of anhydrous tributyl phosphate (TBP). After settling and centrifugation two clear phases were obtained (27.9 g of a first light phase comprising TBP and 2.0 g of intermediate heavy phase comprising water). The heavy phase was re-mixed with 14 g of anhydrous TBP and separated to give 15.4 g of a second light phase comprising TBP and 0.6 g of a final heavy phase comprising water. 98% of the original PDO was found in the combined light phases at a purity of 93.6%, along with 83% of the original glycerol and 37% of the original glucose.

TABLE 3

| | Component Weights | | | Phase Composition % w/w | | | |
| --- | --- | --- | --- | --- | --- | --- | --- |
| | PDO | Glyc | Gluc | PDO | Glyc | Gluc | % DS |
| Feed | 2.009 | 0.150 | 0.027 | 91.9% | 6.9% | 1.2% | 43.7% |
| Light 1 | 1.594 | 0.073 | 0.004 | 95.4% | 4.4% | 0.2% | 6.0% |
| Light 2 | 0.376 | 0.052 | 0.006 | 86.7% | 11.9% | 1.4% | 2.8% |
| Heavy 2 | 0.040 | 0.025 | 0.017 | 48.5% | 30.8% | 20.8% | 13.9% |
| Total lights | 1.970 | 0.125 | 0.010 | 93.6% | 5.9% | 0.5% | |

EXAMPLE 3b

Extraction with Hexanol at 90° C.

In a two stage cross-current extraction scheme, 6.0 g of an aqueous feed at 29.1% dry solids with the composition (% w/w on dry solids) 90.7% PDO, 7.3% glycerol and 2.0% glucose was thoroughly mixed at 90° C. with 18.1 g of hexan-1-ol. After settling and centrifugation two clear phases were obtained (22.1 g of a first light phase comprising hexan-1-ol and 2.0 g of intermediate heavy phase comprising water). The heavy phase was re-mixed with 9.96 g of hexanol and separated to give 11.3 g of a second light phase comprising hexanol and 0.7 g of a final heavy phase comprising water. 97% of the original PDO was found in the combined light phases, along with 75% of the original glycerol and 21% of the original glucose. The purity of the combined light phases was 93.7% (raised from a feed purity of 90.7%)

TABLE 4

| | Component Weights | | | Phase Composition % w/w | | | |
| --- | --- | --- | --- | --- | --- | --- | --- |
| | PDO | Glyc | Gluc | PDO | Glyc | Gluc | % DS |
| Feed | 1.584 | 0.127 | 0.035 | 90.7% | 7.3% | 2.0% | 29.1% |
| Light 1 | 1.261 | 0.058 | 0.003 | 95.4% | 4.4% | 0.2% | 6.0% |
| Light 2 | 0.275 | 0.038 | 0.004 | 86.7% | 11.9% | 1.4% | 2.8% |
| Heavy 2 | 0.048 | 0.031 | 0.027 | 44.8% | 29.4% | 25.7% | 15.2% |
| Total lights | 1.536 | 0.096 | 0.008 | 93.7% | 5.8% | 0.5% | |

EXAMPLE 4

Counter Current Extraction of PDO

EXAMPLE 4a

Robatel Extraction with Broth, Incorporating Purification Step

Figure 9:
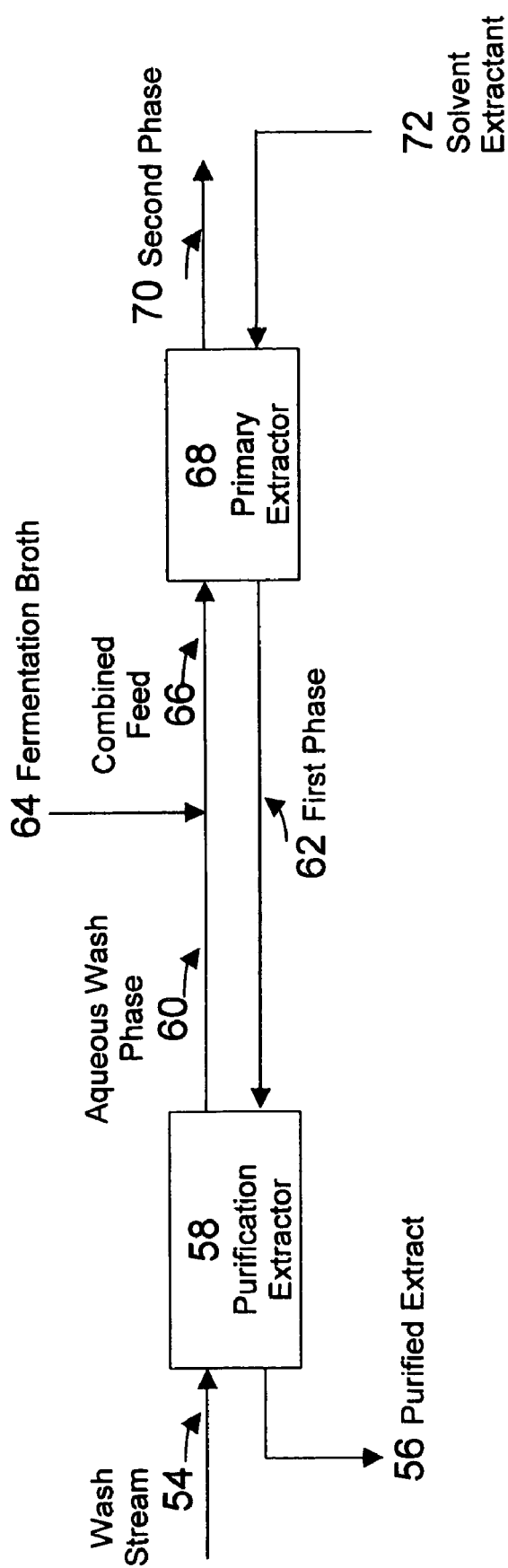
FIG. 9 is a process flow diagram in accordance with the present invention for recovery of 1,3-propanediol involving a washing process.

A laboratory version of a Robatel (an automated sequence of mixer-settlers) was used having 8 mixer-settler stages operating in a counter current fashion in the extraction step and similarly 8 stages in the purification step. FIG. 9 is a representative schematic of the general process used. A fermentation broth 64 is added to a combined feed 66. The combined feed 66 is mixed with solvent extractant 72 in a primary extractor (e.g., Robatel mixer settler) 68. The second phase 70 (e.g., raffinate) comprising water and impurities (e.g., sugars from the fermentation broth) is removed. The first phase 62 comprising solvent extractant and 1,3-propanediol is then washed in a purification extractor 58. The wash stream 54 that is added to the removed first phase 62 can be aqueous, either water or water with the addition of wash chemicals, for example a base such as sodium hydroxide. The purification extractor 58 comprises 8 stages as explained above. The aqueous wash phase 60 can be recovered from the purification extractor 58 leaving a purified extract 56 comprising solvent extractant and purified 1,3-propanediol. The washing or purification with the water 54 can increase the purity of the 1,3-propanediol by removing some impurities, and the aqueous stream comprising water and impurities is combined with fermentation broth 64 in the combined feed 66 and sent back to the main extractor unit 68 in order to reclaim any 1,3-propanediol in the aqueous wash 60, and prevent loss of 1,3-propanediol yield.

The extraction was conducted at ambient temperature. Each stage had a settler volume of 140 ml. The feed was a fermentation broth 64 at about 33% dry solids (d.s.) containing 30.17% w/v of PDO, 1.6% glycerol, 0.7% 1,2,4 butanetriol (BTO) and 0.1% glucose as well as salts of sodium, potassium, calcium & magnesium. The cations totaled 4126 ppm. The broth 64 was fed to the system at 0.85 ml/minute where it was mixed with 0.70 ml/min of purification aqueous outlet stream 60 to give the combined feed 66 at 1.55 ml/min to the extraction step 68. In the extraction step 68 the combined feed 66 was contacted with 14.0 ml/min of wet TBP (tributyl phosphate) 72 (containing 5.4% water). The outputs from the extraction step were a second phase raffinate 70 at 1.1 ml/min and a first phase extract 62 (solvent phase) at 14.45 ml/min. The first phase 62 was contacted with 0.6 ml/min water 54 in the purification stage 58, leading to a purification aqueous outlet stream 60 (led back to the extraction step 68) and 14.35 ml min of purified extract 56 (solvent phase). The analyses are shown in the tables below. The yield of PDO (in the purified extract) was 95% and the purity had been raised from 92.8 to 97.2%. The input of cations was 3200 microgram/minute, with the purified extract representing 255 microgram/minute.

TABLE 5

| | Analysis % w/v | | | | Mass Flow g/min | | | |
|---|---|---|---|---|---|---|---|---|
| | Flow | PDO | Glyc | BTO | Gluc | PDO | Glyc | BTO | Gluc |
| Broth | 0.85 | 31.72 | 1.63 | 0.71 | 0.11 | 0.270 | 0.014 | 0.006 | 0.001 |
| Purified outlet | 0.7 | 15.58 | 1.47 | 0.52 | 0.05 | 0.109 | 0.010 | 0.004 | 0.000 |
| Combined Feed | 1.55 | 26.87 | 1.54 | 0.63 | 1.55 | 0.416 | 0.024 | 0.010 | 0.001 |
| Raffinate | 1.1 | 0.99 | 1.64 | 0.47 | 1.1 | 0.011 | 0.018 | 0.005 | 0.001 |
| Extract | 14.45 | 2.23 | 0.08 | 0.02 | 14.45 | 0.322 | 0.012 | 0.002 | 0.000 |
| Purified Extract | 14.35 | 1.79 | 0.04 | 0.01 | 14.35 | 0.256 | 0.006 | 0.002 | 0.000 |

TABLE 6

| | % On dry matter basis | | | | |
|---|---|---|---|---|---|
| | Flow | PDO | Glyc | BTO | Gluc |
| Broth | 0.85 | 92.8% | 4.8% | 2.1% | 0.3% |
| Purified outlet | 0.7 | 88.4% | 8.3% | 2.9% | 0.3% |
| Combined Feed | 1.55 | 92.2% | 5.3% | 2.2% | 0.3% |

TABLE 6-continued

| | % On dry matter basis | | | | |
|---|---|---|---|---|---|
| | Flow | PDO | Glyc | BTO | Gluc |
| Raffinate | 1.1 | 31.2% | 51.8% | 14.7% | 2.3% |
| Extract | 14.45 | 95.7% | 3.6% | 0.7% | 0.0% |
| Purified Extract | 14.35 | 97.2% | 2.1% | 0.7% | 0.0% |

EXAMPLE 4b

Aqueous Back Extraction of Robatel Purified Extract 16.4 kg of the Purified Extract from Example 4a was mixed with 44.5 kg of reverse osmosis quality water. This water extracts the PDO from the solvent in to the water phase.

This water phase was separated and was mixed with hexane to remove any remaining TBP.

The water phase was then concentrated by evaporation, to produce product with a PDO purity of 97.5%.

TABLE 7

| | % on dry matter basis | | | |
|---|---|---|---|---|
| | PDO | Glyc | BTO | Gluc |
| Aqueous Back Extract | 97.5% | 2.2% | 0.208% | 0.24% |

EXAMPLE 5

Solvent Screens

EXAMPLE 5a

PDO Mixture with Single Solvents 10 g of an aqueous solution containing 46% w/v PDO, 3.5% glycerol and 2.9% glucose was heated to 30° C. and the required solvent added in very small quantities until a cloudiness just began to develop. Additional solvent (about 1 g) was added and thoroughly mixed. The mixture was allowed to settle for 10 minutes and then centrifuged to achieve complete phase separation. The two phases (solvent and aqueous) were analyzed. The table below shows the distribution coefficients of the three species (defined as the concentration in the solvent phase divided by the concentration in the aqueous phase) and the selectivity of extraction of PDO as compared with glycerol (defined as the distribution coefficient of PDO divided by the distribution coefficient of glycerol).

TABLE 8

| Solvent | Distribution Coefficients | | | Selectivity |
| --- | --- | --- | --- | --- |
| | PDO | Glycerol | Glucose | PDO/Glycerol |
| Oleyl Alcohol | 0.038 | 0.024 | 0.001 | 1.60 |
| Hexan-1-ol | 0.326 | 0.134 | 0.029 | 2.43 |
| Tributyl phosphate | 0.203 | 0.077 | 0.016 | 2.65 |
| Butan-1-ol | Only one liquid phase formed | | | |
| Pentan-1-ol | 0.609 | 0.417 | 0.256 | 1.46 |
| 4-Methyl Pentan-2-one | 0.033 | 0.008 | 0.001 | 4.03 |
| isopropyl acetate | 0.024 | 0.005 | 0.001 | 5.17 |
| Oleic acid | 0.009 | 0.002 | 0.241 | 5.23 |

EXAMPLE 5b

Broth with Mixed Solvents 5 ml of a fermentation broth at 33.9% dry material, containing 31.3% w/v PDO, 1.66% glycerol, 0.74% 1,2,4 butanetriol and 0.13% glucose, was extracted at ambient temperature with (usually) 30 ml of a series of solvent mixtures. Two phases were obtained which were separated and analyzed.

TABLE 9

| Solvent | Volumes | | | | Distribution Coefficients | | | | PDO/Glyc Select | PDO Purity |
| --- | --- | --- | --- | --- | --- | --- | --- | --- | --- | --- |
| | Feed | Solvent | Light | Heavy | PDO | Glyc | BTO | Glucose | | |
| Hexanol/TBP | | | | | | | | | | |
| 80/20 | 5 | 30 | 32.5 | 1.2 | 0.23 | 0.03 | 0.01 | 0.00 | 8.8 | 97.2 |
| 50/50 | 5 | 30 | 33 | 1.8 | 0.17 | 0.03 | 0.04 | 0.00 | 6.1 | 97.1 |
| Castor Oil/TBP | | | | | | | | | | |
| 80/20 | 5 | 6 | 6.5 | 4.5 | 0.01 | 0.01 | 0.00 | 0.00 | 2.8 | 98.2 |
| 50/50 | 5 | 6 | 7 | 4 | 0.07 | 0.02 | 0.03 | 0.00 | 4.9 | 97.7 |
| Pentan-1-ol/Hexane | | | | | | | | | | |
| 80/20 | 5 | 30 | 33 | 2 | 0.60 | 0.26 | | 0.26 | 2.3 | |
| 50/50 | 5 | 30 | 33 | 2 | 0.09 | 0.01 | 0.01 | 0.00 | 8.3 | 98.5 |
| Butan-1-ol/Hexane | | | | | | | | | | |
| 80/20 | 5 | 30 | 32.5 | 0.9 | 0.53 | 0.08 | 0.02 | 0.00 | 6.8 | 95.0 |
| 50/50 | 5 | 30 | 33 | 2 | 0.17 | 0.03 | | 0.00 | 5.8 | |
| Pentan-1-ol/Soya oil | | | | | | | | | | |
| 80/20 | 5 | 30 | 32 | 1.2 | 0.30 | 0.06 | | 0.00 | 5.3 | |
| 50/50 | 5 | 30 | 32 | 3 | 0.08 | 0.00 | 0.47 | 0.00 | High | 97.7 |

Glyc—Glycerol. BTO—Butanetriol Select—Selectivity

As before the table shows the distribution coefficients of the species (defined as the concentration in the solvent phase divided by the concentration in the aqueous phase) and the selectivity of extraction of PDO as compared with glycerol (defined as the distribution coefficient of PDO divided by the distribution coefficient of glycerol). In all cases the purity of the extracted PDO is higher than the 92.5% in the feed. The selectivities of the mixed solvents (PDO/glycerol) are often higher than the single solvents shown earlier, and the exclusion of glucose by these solvent mixtures is usually very good.

EXAMPLE 6

Removal of Color and Organic Acids with Alkali

Successive 15 ml portions of a "Purified Extract" (TBP solution) taken from a Robatel counter current extraction and purification of a fermentation broth were mixed with increasing amounts of sodium hydroxide in 1 ml of water. The heavy phases were separated. The color of the heavy (aqueous) phases increased as more alkali was added and that of the light phase decreased. (Light phase color was measured as the absorbance at 300 nm, and heavy phase at 420 nm.) These are shown in the table below. The organic acid levels in the respective sequence of light phases were also measured showing the removal of organic acids as in the table following.

TABLE 10

| mg NaOH | Light Phase | | Heavy Phase | |
| --- | --- | --- | --- | --- |
| Added | pH | Color | pH | Color |
| 0 | 3.5 | 0.124 | 3.85 | 0.004 |
| 2.25 | 4.2 | 0.081 | 6.26 | 0.016 |
| 3.5 | 5.4 | 0.043 | 10.2 | 0.047 |
| 5 | 7.0 | 0.029 | 11.6 | 0.099 |
| 10 | 7.0 | 0.021 | 12.4 | 0.102 |
| 20 | 7.7 | 0.02 | 12.6 | 0.103 |

TABLE 10-continued

| mg NaOH | Light Phase | | Heavy Phase | |
| --- | --- | --- | --- | --- |
| Added | pH | Color | pH | Color |
| 30 | 7.8 | 0.02 | 12.8 | 0.103 |
| 40 | 7.9 | 0.03 | 13.2 | 0.103 |

TABLE 11

| mg NaOH | Light Phase Properties (Acids in ppm w/v) | | | | | |
| --- | --- | --- | --- | --- | --- | --- |
| Added | pH | Lactic | Levul | Acetic | Glycolic | Succinic |
| 0 | 3.5 | 0 | 139 | 378.6 | 11.9 | 0.8 |
| 2.25 | 4.2 | 0 | 50.3 | 238.6 | 11.5 | 1.3 |

TABLE 11-continued

| mg NaOH Added | Light Phase Properties (Acids in ppm w/v) | | | | |
|---|---|---|---|---|---|
| | pH | Lactic | Levul | Acetic | Glycolic | Succinic |
| 3.5 | 5.4 | 0 | 14.1 | 40.7 | 9.3 | 1.4 |
| 5 | 7 | 0 | 6.4 | 41.8 | 1.4 | 0.9 |
| 10 | 7 | 0 | 9.2 | 31.7 | 1.8 | 0.9 |
| 20 | 7.7 | 0 | 9.2 | 35.2 | 1.8 | 1.2 |
| 30 | 7.8 | 0 | 5.9 | 34.1 | 1 | 1.3 |
| 40 | 7.9 | 0 | 18.5 | 82.1 | 3.3 | 1.2 |

"Levul" = Levulinic Acid

EXAMPLE 7

Mixed Bed for Removal of Contaminants

A purified aqueous PDO stream, as in Example 4 after hexane washing, was passed over a 60 ml mixed resin bed and collected in 0.5 bed volume fractions. The mixed bed composition was Purolite C160 Strong Acid Cation resin and Purolite A510 Strong Base Anion resin mixed in a ratio of 1:2 bed volumes. The bed was effective in removing most organic acids as shown in the following table. Levulinic acid was of concern in the original purified sample as it was felt to contribute to the color. As can be seen from the results, the mixed bed was effective at removing most trace acids and the solution remained colorless even after concentration. The color of the feed and concentrate was measured as the absorption at 420 nanometers. The feed color was 0.106, and the concentrate color was zero.

TABLE 12

| | % w/v | | | | ppm w/v | | | | |
|---|---|---|---|---|---|---|---|---|---|
| Fraction | PDO | Glycerol | BTO | Glucose | Lactic | Levul | Acetic | Glycolic | Succinic |
| Feed | 21.98 | 0.208 | 0.2413 | 0.045 | 474 | 37.9 | 42.2 | 35.6 | 244 |
| 0.5BV | 11.63 | 0.130 | 0.11359 | 0 | 0 | 1.4 | 7.4 | 0 | 0 |
| 1.0BV | 18.79 | 0.172 | 0.13388 | 0 | 0 | 1.2 | 8.1 | 1.1 | 0 |
| 1.5BV | 21.06 | 0.211 | 0.17256 | 0 | 0 | 1.2 | 8.4 | 0.7 | 0 |
| 2.0BV | 21.57 | 0.211 | 0.15508 | 0 | 0 | 1.1 | 10.9 | 1.1 | 0 |
| 2.5BV | 21.46 | 0.211 | 0.15732 | 0 | 0 | 1.2 | 10.2 | 0.9 | 0 |
| 3.0BV | 21.47 | 0.212 | 0.15771 | 0 | 0 | 1.1 | 16 | 1.1 | 0 |
| 3.5BV | 21.58 | 0.216 | 0.16117 | 0 | 0 | 1.8 | 18.2 | 1.2 | 0 |
| 4.0BV | 21.82 | 0.229 | 0.1852 | 0 | 0 | 1.5 | 20.8 | 1.7 | 0 |
| Concentrate | 82.73 | 0.784 | 0.5543 | 0 | 0 | 4 | 43 | 3 | 0 |

PDO = 1,3-Propanediol; BTO = 1,2,4 Butanetriol; Levul = Levulinic acid

EXAMPLE 8

Sequential Hexane Extraction 8 ml of a light phase prepared by extracting a fermentation broth with TBP (containing 1.91% w/v of PDO, 0.039% glycerol, 0,085% 1,2,4 butanetriol and no detectable glucose) was contacted with successive portions of n-hexane by mixing, followed by separating the light and heavy phases. After each contact the heavy phases (all about 0.15 ml) were removed before proceeding to the next contact. The analyses of the initial light, and the successive heavy phases are shown in the table below. The earlier aqueous phases were less pure (in terms of PDO) than the feed, and represented 46% of the PDO in the original TBP solution. The aqueous phases from the 4$^{th}$ and 5$^{th}$ extractions were purer in terms of PDO than the feed material.

TABLE 13

| Hexane added | Total hexane | PDO | Glyc | BTO | Gluc | PDO purity | Total PDO* |
|---|---|---|---|---|---|---|---|
| Feed | | 1.91 | 0.04 | 0.08 | 0.00 | 93.9% | |
| 4 | 4 | 15.87 | 0.82 | 0.27 | 0.00 | 93.5% | 16% |
| 4 | 8 | 13.13 | 1.08 | 0.35 | 0.02 | 90.1% | 28% |
| 8 | 16 | 15.35 | 0.84 | 0.27 | 0.00 | 93.3% | 46% |
| 8 | 24 | 17.10 | 0.63 | 0.23 | 0.00 | 95.3% | 60% |
| 16 | 40 | 19.02 | 0.42 | 0.20 | 0.00 | 96.9% | 79% |

*Cumulative PDO extracted into aqueous phases

EXAMPLE 9

Sequential Water Extraction 20 ml of a first phase prepared by extracting a fermentation broth with TBP (containing 1.91% w/v of PDO, 0.039% glycerol, 0,085% 1,2,4 butanetriol and no detectable glucose) was contacted with six successive 2 ml portions of water by mixing, followed by separating the light and heavy phases. After each contact the heavy phases (all about 2 ml) were removed before proceeding to the next contact. The analyses of the initial light, and the successive heavy phases are shown in the table below. The purity of the aqueous phases increase with successive extractions.

TABLE 14

| Water added (ml) | Total water (ml) | PDO | Glyc | BTO | Gluc | PDO purity | Total PDO* |
|---|---|---|---|---|---|---|---|
| Feed | | 1.91 | 0.04 | 0.08 | 0.00 | 93.9% | |
| 2 | 2 | 8.083 | 0.310 | 0.193 | 0.00 | 94.1% | 42.2% |
| 2 | 4 | 4.182 | 0.102 | 0.107 | 0.02 | 95.2% | 64.1% |
| 2 | 6 | 2.025 | 0.010 | 0.014 | 0.00 | 98.8% | 74.7% |
| 2 | 8 | 0.902 | 0.002 | 0.007 | 0.00 | 99.0% | 79.4% |
| 2 | 10 | 0.417 | 0.000 | 0.004 | 0.00 | 99.1% | 81.6% |
| 2 | 12 | 0.176 | 0.002 | 0.005 | 0.00 | 96.3% | 82.5% |

*Cumulative PDO extracted into aqueous phases

EXAMPLE 10

5 g of fermentation broth at 55% dry solids PDO, was added to 30 g of tributyl phosphate (TBP) containing varying percentages of kerosene, from 0 to 50%. The mixtures were mixed carefully so as not to create micro bubbles and the time taken for phase separation was noted.

Table 15 shows that the increase in kerosene percentage in the TBP extracting solvent speeds up the phase separation between the aqueous and solvent phases. At 100% TBP extracting solvent the rate is 5 minutes for complete separation, at 80% TBP and 20% kerosene it has decreased to 3 minutes (a 40% reduction), at 50% TBP and kerosene the rate has decreased to 1.5 minutes (a 70% reduction).

Table 15

Settling rates as a function of time at 20° C. for fermentation broth (at 55% dry solids PDO) and TBP/kerosene mixtures at 6 (solvent):1 (broth) Ratio

| | Time 1 minute | Time 5 minute |
|---|---|---|
| TBP 100% | Top & bottom layers separate Top layer very fine cloudy approx. 2% | Bottom layer clear & reads 5 ml on graduated tube Top layer all clear no visible bubbles |
| | | Time 3 minute |
| TBP 80% Kerosene 20% | Time 1 minute Top & bottom layers separate Top layer very fine cloudy approx. 1% | Bottom layer clear & reads 5 ml on graduated tube Top layer all clear no visible bubbles |
| | | Time 1.5 minute |
| TBP 50% Kerosene 50% | Time 1 minute Top & bottom layers separate Top layer very fine cloudy approx. 1% | Bottom layer clear & reads 5 ml on graduated tube Top layer all clear no visible bubbles |

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for the recovery of 1,3-propanediol from a fermentation broth comprising 1,3-propanediol, comprising the steps of:
    contacting a fermentation broth that comprises greater than about 10 wt % water, about 5-85 wt % 1,3-propanediol, and about 5-70 wt % of at least one contaminant selected from glycerol, glucose, and butanetriol, with at least one solvent extractant to form a first mixture, wherein the solvent extractant is selected from the group consisting of pentanol, propan-1-ol, hexanol, oleyl alcohol, 4-methyl pentan-2-one, isopropyl acetate, tributyl phosphate, oleic acid, soya oil, castor oil, and combinations thereof, and wherein the volume/volume ratio of solvent extractant to fermentation broth is between 1:4 and 50:1,
    separating the first mixture into a first phase and a second phase,
    wherein the first phase comprises a majority of the solvent extractant and at least some of the 1,3-propanediol that was present in the fermentation broth, and the weight ratio in the first phase of 1,3-propanediol to at least one of glycerol, glucose, or butanetriol is greater than the weight ratio of 1,3-propanediol to the same contaminant in the fermentation broth prior to the fermentation broth being contacted with the solvent extractant,
    wherein the second phase comprises a majority of the water and at least some of the contaminant from the fermentation broth,
    recovering 1,3-propanediol by removing the first phase from the second phase,
    contacting the removed first phase with a first quantity of aqueous solution to form a second mixture, wherein the volume ratio of the first quantity of aqueous solution to the first phase is between about 20:1 and about 1:20, and
    separating the second mixture into a third phase and a fourth phase,
    wherein the third phase comprises a majority of solvent extractant of the first phase, and wherein the fourth phase comprises 1,3-propanediol and a majority of the first quantity of aqueous solution, the weight ratio in the fourth phase of the 1,3-propanediol to at least one of glycerol, glucose, or butanetriol is greater than the weight ratio of 1,3-propanediol to the same contaminant in the fermentation broth prior to the fermentation broth being contacted with the solvent extractant, and said contacting and recovering steps result in the concentration of 1,3 propanediol in the fourth phase being over 99 wt % on a water-excluded basis.

2. The process of claim 1, wherein the volume ratio is between about 20:1 and 1:1.

3. The process of claim 1, wherein the volume ratio is about 7:1 to 3:1.

4. The process of claim 1, wherein the fermentation broth is concentrated to at least about 90 wt % d.s.

5. The process of claim 1, wherein the fermentation broth is partially purified.

6. The process of claim 1, wherein the fermentation broth has a pH of between about 2 and 11.

7. The process of claim 1, wherein the fermentation broth has a pH of between about 6 and 8.

8. The process of claim 1, wherein the fermentation broth comprises between about 20 wt % and 80 wt % dry solids.

9. The process of claim 1, wherein the process is carried out at a temperature between about 20° C. and 90° C.

10. The process of claim 1, wherein the process is carried out at a temperature between about 25° C. and 35° C.

11. The process of claim 1, wherein the solvent extractant is essentially anhydrous.

12. The process of claim 1, wherein the solvent extractant is saturated with water.

13. The process of claim 1, wherein the solvent extractant is selected from the group consisting of hexanol and tributyl phosphate.

14. The process of claim 1, wherein the first mixture comprises a phase enhancer selected from the group consisting of aliphatic and aromatic hydrocarbons.

15. The process of claim 14, wherein the phase enhancer is an alkane having between 6 and 10 carbon atoms.

16. The process of claim 1, wherein the solvent extractant comprises carbon and oxygen atoms in a ratio of between about 2:1 and 18:1.

17. The process of claim 16, wherein the solvent extractant comprises carbon and oxygen atoms in a ratio of between about 3:1 and 6:1.

18. A process for the recovery of 1,3-propanediol from a fermentation broth comprising 1,3-propanediol, comprising the steps of:
contacting a fermentation broth that comprises greater than about 10 wt % water, about 5-85 wt % 1,3-propanediol, and about 5-70 wt % of at least one contaminant selected from glycerol, glucose, and butanetriol, with at least one solvent extractant to form a first mixture, wherein the solvent extractant is selected from the group consisting of pentanol, propan-1-ol, hexanol, oleyl alcohol, 4-methyl pentan-2-one, isopropyl acetate, tributyl phosphate, oleic acid, soya oil, castor oil, and combinations thereof, and wherein the volume/volume ratio of solvent extractant to fermentation broth is between 1:4 and 50:1,
separating the first mixture into a first phase and a second phase, wherein the first phase comprises a majority of the solvent extractant and at least some of the 1,3-propanediol that was present in the fermentation broth, and the weight ratio in the first phase of 1,3-propanediol to at least one of glycerol, glucose, or butanetriol is greater than the weight ratio of 1,3-propanediol to the same contaminant in the fermentation broth prior to the fermentation broth being contacted with the solvent extractant, and wherein the second phase comprises a majority of the water and at least some of the contaminant from the fermentation broth,
recovering 1,3-propanediol by removing the first phase from the second phase,
contacting the removed first phase with a first quantity of aqueous solution to form a second mixture, wherein the volume ratio of the first quantity of aqueous solution to the first phase is between about 20:1 and about 1:20, and
separating the second mixture into a third phase and a fourth phase, wherein the third phase comprises a majority of solvent extractant of the first phase, and wherein the fourth phase comprises 1,3-propanediol and a majority of the first quantity of aqueous solution, the weight ratio in the fourth phase of the 1,3-propanediol to at least one of glycerol, glucose, or butanetriol is greater than the weight ratio of 1,3-propanediol to the same contaminant in the fermentation broth prior to the fermentation broth being contacted with the solvent extractant, and said contacting and recovering steps result in the concentration of 1,3 propanediol in the fourth phase being over 99 wt % on a water-excluded basis, and
recovering 1,3-propanediol by removing the fourth phase from the third phase.

19. A process for the recovery of 1,3-propanediol from a fermentation broth comprising 1,3-propanediol, comprising the steps of:
contacting a fermentation broth that comprises greater than about 10 wt % water, about 5-85 wt % 1,3-propanediol, and about 5-70 wt % of at least one contaminant selected from glycerol, glucose, and butanetriol, with at least one solvent extractant to form a first mixture, wherein the solvent extractant is selected from the group consisting of pentanol, propan-1-ol, hexanol, oleyl alcohol, 4-methyl pentan-2-one, isopropyl acetate, tributyl phosphate, oleic acid, soya oil, castor oil, and combinations thereof, and wherein the volume/volume ratio of solvent extractant to fermentation broth is between 1:4 and 50:1,
separating the first mixture into a first phase and a second phase, wherein the first phase comprises a majority of the solvent extractant and at least some of the 1,3-propanediol that was present in the fermentation broth, and the weight ratio in the first phase of 1,3-propanediol to at least one of glycerol, glucose, or butanetriol is greater than the weight ratio of 1,3-propanediol to the same contaminant in the fermentation broth prior to the fermentation broth being contacted with the solvent extractant, and wherein the second phase comprises a majority of the water and at least some of the contaminant from the fermentation broth,
recovering 1,3-propanediol by removing the first phase from the second phase,
contacting the removed first phase with a first quantity of aqueous solution to form a second mixture, wherein the volume ratio of the first quantity of aqueous solution to the first phase is between about 20:1 and about 1:20, and
separating the second mixture into a third phase and a fourth phase, wherein the third phase comprises a majority of solvent extractant of the first phase, and wherein the fourth phase comprises 1,3-propanediol and a majority of the first quantity of aqueous solution, the weight ratio in the fourth phase of the 1,3-propanediol to at least one of glycerol, glucose, or butanetriol is greater than the weight ratio of 1,3-propanediol to the same contaminant in the fermentation broth prior to the fermentation broth being contacted with the solvent extractant, and said contacting and recovering steps result in the concentration of 1,3 propanediol in the fourth phase being over 99 wt % on a water-excluded basis,
recovering 1,3-propanediol by removing the fourth phase from the third phase, and
recycling the recovered third phase such that the solvent extractant comprises the recovered third phase.

20. A process for the recovery of 1,3-propanediol from a fermentation broth comprising 1,3-propanediol, comprising the steps of:
contacting a fermentation broth that comprises greater than about 10 wt % water, about 5-85 wt % 1,3-propanediol, and about 5-70 wt % of at least one contaminant selected from glycerol, glucose, and butanetriol, with at least one solvent extractant to form a first mixture, wherein the solvent extractant is selected from the group consisting of pentanol, propan-1-ol, hexanol, oleyl alcohol, 4-methyl pentan-2-one, isopropyl acetate, tributyl phosphate, oleic acid, soya oil, castor oil, and combinations thereof, and wherein the volume/volume ratio of solvent extractant to fermentation broth is between 1:4 and 50:1,
separating the first mixture into a first phase and a second phase, wherein the first phase comprises a majority of the solvent extractant and at least some of the 1,3-propanediol that was present in the fermentation broth, and the weight ratio in the first phase of 1,3-propanediol to at least one of glycerol, glucose, or butanetriol is greater than the weight ratio of 1,3-propanediol to the same contaminant in the fermentation broth prior to the fermentation broth being contacted with the solvent extractant, and wherein the second phase comprises a majority of the water and at least some of the contaminant from the fermentation broth,
recovering 1,3-propanediol by removing the first phase from the second phase,
contacting the removed first phase with a first quantity of aqueous solution to form a second mixture, wherein the volume ratio of the first quantity of aqueous solution to the first phase is between about 20:1 and about 1:20, and separating the second mixture into a third phase and a fourth phase, wherein the third phase comprises a majority of solvent extractant of the first phase, and wherein the fourth phase comprises 1,3-propanediol and a majority of the first quantity of aqueous solution, the weight ratio in the fourth phase of the 1,3-propanediol to at least one of glycerol, glucose, or butanetriol is greater than the weight ratio of 1,3-propanediol to the same contaminant in the fermentation broth prior to the fermentation broth being contacted with the solvent extractant, and said contacting and recovering steps result in the concentration of 1,3 propanediol in the fourth phase being over 99 wt % on a water-excluded basis, recovering 1,3-propanediol by removing the fourth phase from the third phase, and treating the recovered fourth phase to further purify 1,3-propanediol in the fourth phase.

21. A process for the recovery of 1,3-propanediol from a fermentation broth comprising 1,3-propanediol, comprising the steps of:

contacting a fermentation broth that comprises greater than about 10 wt % water, about 5-85 wt % 1,3-propanediol, and about 5-70 wt % of at least one contaminant selected from glycerol, glucose, and butanetriol, with at least one solvent extractant to form a first mixture, wherein the solvent extractant is selected from the group consisting of pentanol, propan-1-ol, hexanol, oleyl alcohol, 4-methyl pentan-2-one, isopropyl acetate, tributyl phosphate, oleic acid, soya oil, castor oil, and combinations thereof, and wherein the volume/volume ratio of solvent extractant to fermentation broth is between 1:4 and 50:1, separating the first mixture into a first phase and a second phase, wherein the first phase comprises a majority of the solvent extractant and at least some of the 1,3-propanediol that was present in the fermentation broth, and the weight ratio in the first phase of 1,3-propanediol to at least one of glycerol, glucose, or butanetriol is greater than the weight ratio of 1,3-propanediol to the same contaminant in the fermentation broth prior to the fermentation broth being contacted with the solvent extractant, and wherein the second phase comprises a majority of the water and at least some of the contaminant from the fermentation broth, recovering 1,3-propanediol by removing the first phase from the second phase, contacting the removed first phase with a first quantity of aqueous solution to form a second mixture, wherein the volume ratio of the first quantity of aqueous solution to the first phase is between about 20:1 and about 1:20, and separating the second mixture into a third phase and a fourth phase, wherein the third phase comprises a majority of solvent extractant of the first phase, and wherein the fourth phase comprises 1,3-propanediol and a majority of the first quantity of aqueous solution, the weight ratio in the fourth phase of the 1,3-propanediol to at least one of glycerol, glucose, or butanetriol is greater than the weight ratio of 1,3-propanediol to the same contaminant in the fermentation broth prior to the fermentation broth being contacted with the solvent extractant, and said contacting and recovering steps result in the concentration of 1,3 propanediol in the fourth phase being over 99 wt % on a water-excluded basis, recovering 1,3-propanediol by removing the fourth phase from the third phase, and recycling the fourth phase such that the fermentation broth comprises the recovered fourth phase.

* * * * *